(12) United States Patent
Nisisako et al.

(10) Patent No.: US 8,961,898 B2
(45) Date of Patent: Feb. 24, 2015

(54) METHOD FOR PRODUCING BILAYER MEMBRANE AND PLANAR BILAYER MEMBRANE

(75) Inventors: Takasi Nisisako, Yokohama (JP); Takahiro Baba, Yokohama (JP)

(73) Assignee: Tokyo Institute of Technology, Tokyo (JP)

( * ) Notice: Subject to any disclaimer, the term of this patent is extended or adjusted under 35 U.S.C. 154(b) by 750 days.

(21) Appl. No.: 12/450,517

(22) PCT Filed: Mar. 28, 2008

(86) PCT No.: PCT/JP2008/056737
§ 371 (c)(1),
(2), (4) Date: Feb. 19, 2010

(87) PCT Pub. No.: WO2008/120816
PCT Pub. Date: Oct. 9, 2008

(65) Prior Publication Data
US 2010/0148123 A1   Jun. 17, 2010

(30) Foreign Application Priority Data

Mar. 30, 2007  (JP) ................................ 2007-094443

(51) Int. Cl.
*B01L 3/00* (2006.01)
*G01N 33/487* (2006.01)
(Continued)

(52) U.S. Cl.
CPC ......... *B01L 3/502784* (2013.01); *B01L 3/5027* (2013.01); *G01N 27/44791* (2013.01);
(Continued)

(58) Field of Classification Search
CPC ................... C12Q 2565/631; C12Q 2565/629; B01L 3/5027; B01L 2300/0819; B01L 2300/0864; B01L 2300/0829; B01L 3/5085; B01L 2200/0636; B01L 2300/0816; B01J 19/0046; C12M 23/16; G01N 27/44791
USPC .................. 422/245.1, 400, 82.01, 52, 82.05, 422/82.06, 82.07, 82.08, 82.09, 82.11, 407, 422/500, 501, 50, 2, 503, 504, 930; 436/52, 436/53, 164, 165, 172, 174, 518, 524, 525, 436/526, 805, 809; 435/287.1, 6.11, 7.1, 435/164, 165, 283.1, 287.2, 288.7, 808, 4, 435/5, 7.2, 7.9; 204/403.01, 540; 205/777.5; 210/639, 645; 252/408.1; 264/212, 553; 424/427; 604/4.01
See application file for complete search history.

(56) References Cited

U.S. PATENT DOCUMENTS

2005/0032240 A1 * 2/2005 Lee et al. ...................... 436/180

FOREIGN PATENT DOCUMENTS

JP   3-35792 A   2/1991
JP   7-173052 A  7/1995
(Continued)

OTHER PUBLICATIONS

Funakoshi et al , "Lipid Bilayer Formation by Contacting Monolayers in a Microfluidic Device for Membrane Protein Analysis" Anal. Chem. 2006, 78, 8169-8174.*
(Continued)

*Primary Examiner* — Dennis M White
(74) *Attorney, Agent, or Firm* — Foley & Lardner LLP

(57) ABSTRACT

The present invention provides a bilayer membrane produced using a microchannel capable of easily forming bilayer membranes such as planar lipid bilayer membranes in large quantities, and a production method thereof. A process for producing a bilayer membrane of the present invention comprises forming a state where two liquid phases or liquid and gaseous phases each containing amphipathic molecules are alternately arranged in a microchannel, discharging one of the two liquid phases or the gaseous phase of the liquid and gaseous phases through branch minichannels formed in the wall on one side or in the walls on both sides to contact the remaining liquid phases adjacent to each other, and thereby forming a side-by-side arrangement of bilayer membranes comprising the amphipathic molecules.

21 Claims, 12 Drawing Sheets

(51) Int. Cl.
G01N 27/447 (2006.01)
C12M 3/06 (2006.01)

(52) U.S. Cl.
CPC ......... *B01L2200/0636* (2013.01); *C12M 23/16* (2013.01); *B01L 3/502753* (2013.01); *B01L 2300/0816* (2013.01); *B01L 2300/0864* (2013.01); *G01N 33/48728* (2013.01); *Y10S 435/808* (2013.01); *Y10S 436/805* (2013.01); *Y10S 436/809* (2013.01)
USPC ....... 422/502; 422/52; 422/82.05; 422/82.06; 422/82.07; 422/82.08; 422/82.09; 422/82.11; 422/407; 422/500; 422/501; 422/503; 422/504; 422/930; 435/164; 435/165; 435/283.1; 435/287.1; 435/287.2; 435/288.7; 435/808; 435/4; 435/5; 435/7.2; 435/7.9; 436/52; 436/53; 436/164; 436/165; 436/174; 436/518; 436/524; 436/525; 436/526; 436/805; 436/809

(56) References Cited

FOREIGN PATENT DOCUMENTS

| | | |
|---|---|---|
| JP | 2004-59802 A | 2/2004 |
| JP | 2004-351417 A | 12/2004 |
| JP | 2005-91305 A | 4/2005 |
| JP | 2005-98718 A | 4/2005 |
| JP | 2005-315832 A | 11/2005 |
| WO | WO 2007/013493 A1 | 2/2007 |

OTHER PUBLICATIONS

Moran-Mirabal et al ("Micrometer-Sized Supported Lipid Bilayer Arrays for Bacterial Toxin Binding Studies through Total Internal Reflection Fluorescence Microscopy." Biophysical Journal, vol. 89, Jul. 2005, pp. 296-305.*
International Search Report of May 13, 2008, in prior PCT/JP2008/056737, 2 pages.
Baba et al., "Micro Ryuro ni Okeru Ekiteki Zengo Sesshoku o Mochiita Shishitsu Heimenmaku no Heiretsu Seisei Gijutsu," Dai 15 Kai Society for Chemistry and Micro-Nano Systems Koen Yoshishu, May 25, 2007, p. 39, 2 pages.
Baba et al., "Micro Ryuronai no Ekiteki Zengo Sesshoku o Riyo shita Shishitsu Heimenmaku no Heiretsu Keisei," 2007 Nendo Seimitsu Kogakukai Shuki Taikai Gakujutsu Koenkai Koen Ronbunshu, Sep. 3, 2007, 837-838, 3 pages.
Malmstadt et al., "Automated Formation of Lipid-Bilayer Membranes in a Microfluidic Device," Nano Letters, 2006, 6(9):1961-1965.
Takeuchi, Shoji, "Membrane protein chips," Applied Physics, 2005, 74:1589-1593.

* cited by examiner

METHOD FOR PRODUCING BILAYER MEMBRANE AND PLANAR BILAYER MEMBRANE

CROSS-REFERENCE TO RELATED APPLICATIONS

This application is a National Stage application of PCT/JP2008/056737, filed Mar. 28, 2008, which claims priority from Japanese application JP 2007-094443, filed Mar. 30, 2007.

TECHNICAL FIELD

The present invention relates to a method for producing a bilayer membrane and a planer bilayer membrane produced thereby.

PRIOR ART

Now, in the post-genome era, the analyses of protein structures and functions are actively studied domestically and abroad. Recently, the elucidation of functions of "membrane proteins", which are specifically embedded in cell membranes and are responsible for information exchange and energy conversion inside and outside the membranes, has attracted attention in hope of the elucidation of various disease mechanisms and the development of new drugs.

Function analysis methods include an electrophysiological technique in which a purified membrane protein is immobilized in an artificial phosphatide bilayer membrane. For a rapid function analysis of membrane proteins, it is desirable to comprehensively investigate conditions (screening) by arranging a large number of lipid bilayer membranes side by side. Also, studies of various biosensors using planar lipid bilayer membranes have been reported.

A technique using LB (Langmuir-Blodgett) membranes is one of the methods for forming lipid bilayer membranes commonly used in the art. Also, some studies have been recently reported to form lipid bilayer membranes using a structure fabricated by a microfabrication technique (e.g., Takeuchi, Applied Physics 74, 1589 (2005) and N. Malmstadt et al., Nono letters 6, 1961 (2006)).

However, techniques in the art for forming lipid bilayer membranes require a lot of effort, and are not suitable for efficiently forming a large number of membranes. Therefore, it is difficult to apply a technique in the art for forming lipid bilayer membranes to the formation of planar lipid bilayer membranes for screening.

DISCLOSURE OF THE INVENTION

In light of the above, the object of the present invention is to provide a process for forming a bilayer membrane with a microchannel capable of easily forming bilayer membranes such as planar lipid bilayer membranes in large quantities, and a planar bilayer membrane obtained thereby.

The present invention provides the following inventions to solve the above problems.

(1) A process for producing a bilayer membrane, comprising: forming a state where two liquid phases or liquid and gaseous phases each containing amphipathic molecules are alternately arranged in a microchannel, discharging one of the two liquid phases or the gaseous phase of the liquid and gaseous phases through branch minichannels formed in the wall on one side or in the walls on both sides to contact the remaining liquid phases adjacent to each other, and thereby forming a side-by-side arrangement of bilayer membranes comprising the amphipathic molecules.

(2) A process for producing a bilayer membrane according to the above (1), comprising: alternately introducing two liquid phases or liquid and gaseous phases each containing amphipathic molecules using a branch structure of the microchannel to form the state where the two liquid phases or liquid and gaseous phases each containing amphipathic molecules are alternately arranged.

(3) A process for producing a bilayer membrane according to the above (2), wherein the branch structure of a microchannel is selected from a cross-shaped intersection, T-shaped intersection, and Y-shaped intersection.

(4) A process for producing a bilayer membrane according to any one of the above (1) to (3), wherein the two liquid phases are an organic phase and a water phase.

(5) A process for producing a bilayer membrane according to any one of the above (1) to (3), the amphipathic molecules are a lipid, surfactant, or polymer.

(6) A process for producing a bilayer membrane according to the above (4) or (5), wherein the amphipathic molecules are introduced in admixture with the organic phase.

(7) A process for producing a bilayer membrane according to any one of the above (1) to (3), wherein the amphipathic molecules are adsorbed on an interface of the organic phase and the water phase to form a monolayer membrane.

(8) A process for producing a bilayer membrane according to any one of the above (4) to (7), comprising discharging the organic phase through branch minichannels formed in the wall on one side or in the walls on both sides to contact the water phases adjacent to each other.

(9) A process for producing a bilayer membrane according to any one of the above (4) to (7), comprising discharging the water phase through branch minichannels formed in the wall on one side or in the walls on both sides to contact the organic phases adjacent to each other.

(10) A process for producing a bilayer membrane according to any one of the above (1) to (9), wherein the discharge through branch minichannels is performed by capillary action and/or suction.

(11) A process for producing a bilayer membrane according to any one of the above (1) to (10), wherein two or more bilayer membranes have a side-by-side arrangement at a constant interval.

(12) A process for producing a bilayer membrane according to any one of the above (1) to (11), wherein the bilayer membrane is sandwiched with liquid phases comprising different components.

(13) A bilayer membrane having a side-by-side arrangement of two or more bilayer membranes and comprising amphipathic molecules.

(14) A bilayer membrane according to the above (13), wherein the side-by-side arrangement is formed via an organic or water phase.

(15) A bilayer membrane according to the above (13) or (14), wherein the bilayer is sandwiched with liquid phases comprising different components.

(16) A bilayer membrane, wherein one or more bilayer membranes comprising amphipathic molecules are provided in a microchannel.

(17) A bilayer membrane according to the above (16), two or more bilayer membranes are arranged side by side.

(18) A bilayer membrane according to any one of the above (13) to (17), wherein the amphipathic molecules are a phosphatide.

(19) A bilayer membrane according to the above (18), wherein a biological molecule is immobilized in the phosphatide.

(20) A bilayer membrane according to the above (19), wherein the biological molecule is a membrane protein.

(21) A bilayer membrane according to the above (20), wherein the membrane protein is selected from one ox more of ion channel proteins, transporters, ion pump proteins and receptors.

(22) A device comprising the bilayer membrane according to any one of the above (13) to (21).

(23) A device according to the above (22), wherein the device is a function analysis device of membrane proteins.

(24) A device according to the above (22), wherein the device is a sensor device.

The present invention provides a process for forming a bilayer membrane with a microchannel capable of easily forming bilayer membranes such as planar lipid bilayer membranes in large quantities, and a planar bilayer membrane obtained thereby.

For example, a side-by-side arrangement of bilayer membranes can be formed by forming a plug flow consisting of an organic phase comprising a phosphatide and a water phase in a hydrophobic channel, and discharging the organic phase through a microchannel on a wall surface to contact water phases adjacent to each other. A membrane protein can be immobilized in a bilayer membrane by blending the membrane protein with an organic phase or a water phase. Furthermore, a function analysis of proteins can be performed if microelectrodes are inserted in the microchannel.

BEST MODE FOR CARRYING OUT THE INVENTION

Figure 1:
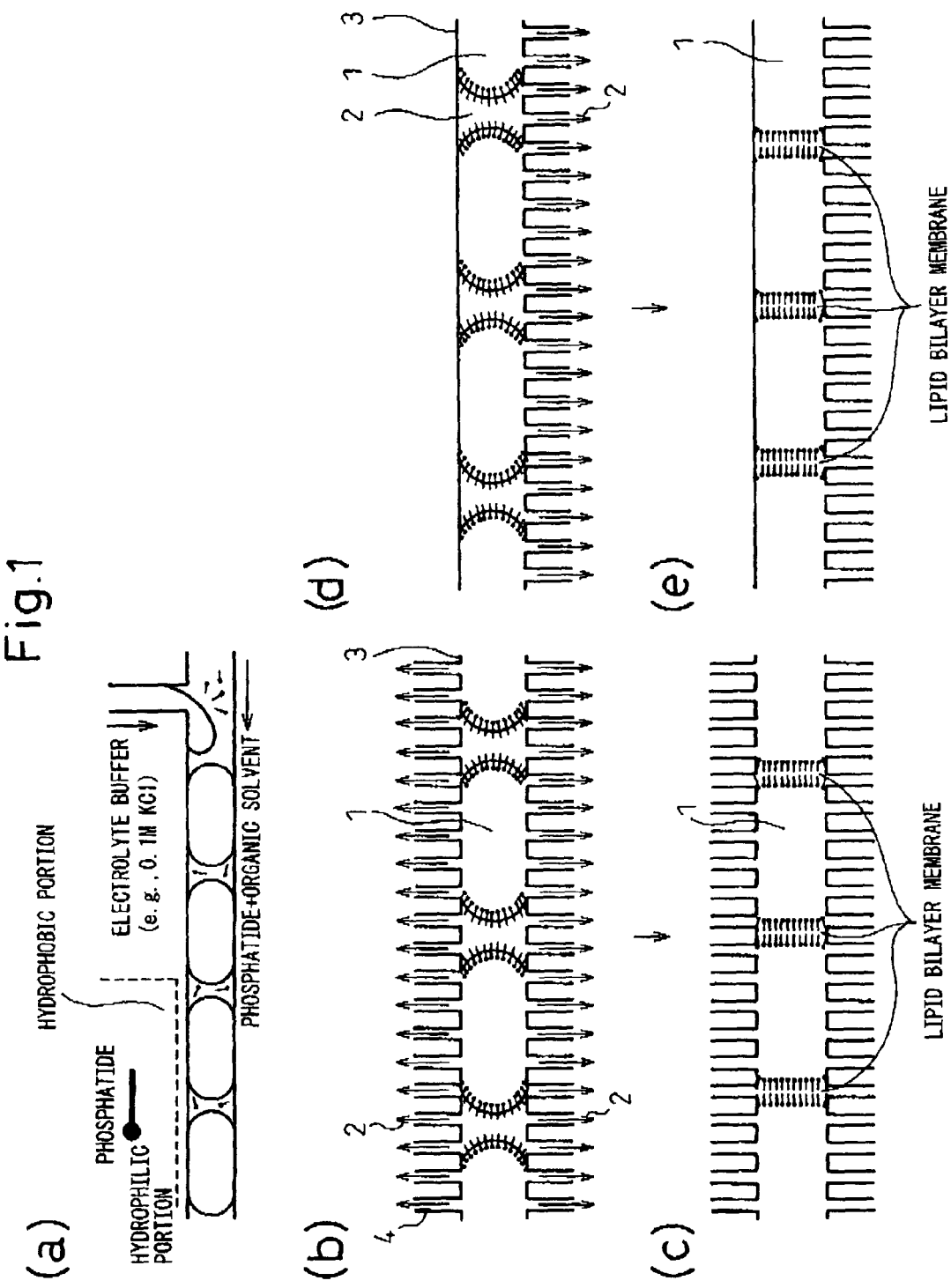
FIG. 1 shows a schematic diagram of producing a planar bilayer membrane of the present invention.

The process for producing a bilayer membrane according to the present invention comprises: forming a state where two liquid phases or liquid and gaseous phases each containing amphipathic molecules are alternately arranged in a microchannel, discharging one of the two liquid phases or the gaseous phase of the liquid and gaseous phases through branch minichannels formed in the wall on one side or in the walls on both sides to contact the remaining liquid phases adjacent to each other, and thereby forming a side-by-side arrangement of bilayer membranes comprising the amphipathic molecules.

Examples of the two liquid phases include, an organic phase and a water phase, and two organic phases having different polar characters (e.g., one aqueous solvent having a large polarity, and one oily solvent having a small polarity). Examples of the organic phase include various organic compounds, preferably, alkanes such as decane, octane; halogenated hydrocarbons such as chloroform; aromatic hydrocarbons such as toluene; aliphatic acids such as oleic acid. When a liquid phase and a gaseous phase are used, preferably, the liquid phase is an organic phase or a water phase while the gaseous phase is air, nitrogen, argon, helium.

Examples of amphipathic molecules generally include a lipid such as phosphatide, glycolipid, neutral lipid; amphipathic surfactant such as palmitic acid, stearic acid; polymer such as a block copolymer having in its structure a hydrophobic portion and a hydrophilic portion. Examples of such a block copolymer include poly(ethylene oxide)-polyethylethylene, poly(ethylene oxide)-polybutadiene, polystyrene-polyacrylate, poly(ethylene oxide)-polycaprolactam, poly(butyl acrylate)-polyacrylate.

It is preferable to form a state, where two liquid phases or a liquid phase and a gaseous phase each having amphipathic molecules are alternately arranged, by alternately discharging the two liquid phases or the liquid phase and the gaseous phase each having amphipathic molecules through a branch structure of a microchannel. Such a branch structure of a microchannel is preferably selected from, but not limited to, a cross-shaped intersection, T-shaped intersection, and Y-shaped intersection. The size of the microchannel can be determined according to the object, but is normally about 1 to 1,000 μm, preferably about 10 to 500 μm. The material to form the microchannel may be, for example, any one of plastics, ceramics, metals, etc.; preferably, an acrylate resin or silicone resin in the case of a hydrophobic wall surface of the microchannel; and, preferably, fused silica, silicon, borosilicate glass (e.g., "Pyrex (registered trademark)" (brand name)) in the case of a hydrophilic wall surface. The shape and size of the material to form the microchannel can be appropriately determined according to the usage, and may be a plate-like body (e.g., a few centimeter cube) having a fabricated channel.

Amphipathic molecules are preferably introduced in admixture with an organic phase. The amphipathic molecules are adsorbed onto an interface between two liquid phases (e.g., an organic phase and a water phase) or a liquid phase and a gaseous phase, to form a monolayer membrane. As shown FIG. 3 below, an asymmetrical bilayer membrane can be formed by introducing different amphipathic molecules in an organic phase divided into two parts.

In order to control the state where two liquid phases or a liquid phase and a water phase each having amphipathic molecules are alternately arranged, for example, the above branch structure of the microchannel can be used for the supply. Depending on the viscosity, surface tension, density, liquid properties (polarity), etc. of the two liquid phases, the discharge rate (discharge amount) of the two liquid phases can be appropriately determined. In such a case, a continuous phase and a dispersed phase (droplet) can be formed by the methods according to Japanese Unexamined Patent Publication (Kokai) No. 2004-12402, Kokai No. 2004-67953, Kokai No. 2004-59802, Kokai No. 2005-255987, and Kokai No. 2005-270894.

If the two liquid phases are an organic phase and a water phase, a bilayer membrane can be preferably formed by introducing the organic phase through branch minichannels formed in the wall on one side or in the walls on both sides to contact the water phases adjacent to each other, and binding monolayers.

A bilayer of the present invention may be sandwiched with liquid phases comprising different components, such as a water phase and an organic phase, or water phases comprising different components (e.g., Example 3 below) or organic phases. In such a case, an experimental system can be formed which represents the inside and outside portions of cells.

The branch minichannels are formed in the wall on one side or in the walls on both sides of the microchannel to discharge one of the liquid phases, as mentioned above, by capillary action (voluntary osmosis) and/or suction (with a pump or valve). The size of the branch minichannels can be appropriately determined from the range suitable for the capillary action and/or suction, and is generally selected from approximately 0.1 to 200 μm.

The present invention provides a bilayer membrane having a structure in which the bilayer membrane is provided in the microchannel (or space which is used to be a microchannel) and comprising amphipathic molecules. Generally, two or more bilayer membranes are arranged side by side at intervals. The intervals can be determined according to the purpose, and is formed via an organic phase or a water phase. Between the organic phases and the water phases, a bilayer membrane comprising amphipathic molecules is provided. The bilayer membrane may be sandwiched with liquid phases having different components. However, the intervals may be zero (i.e., multilayer membrane) by removing the organic phase or a water phase, or a mixed type of a bilayer membrane and a multilayer membrane. Only one bilayer membrane may be provided in the organic phase or the water phase in the microchannel (or space which is used to be a microchannel).

The bilayer membrane may be planar or spherical. It may be a closed sphere, but a planar bilayer membrane is generally selected.

If the amphipathic molecules are, for example, a phosphatide, a bilayer membrane on which biological molecules such as membrane proteins are immobilized can be formed by blending the biological molecules with the organic phase or the water phase. Examples of the membrane protein include one or more of ion channel proteins, transporters, ion pump proteins and receptors.

For example, an ion channel protein has a function of penetrating ions according to the gradient of the electrochemical potential. In a planar bilayer membrane incorporated with the ion channel protein, the ion current can be electrophysiologically measured. A transporter is a carrier, which transports organic substances such as glucides and amino acids. Examples thereof include an ABC transporter which has an ATP binding cassette and an ABC hydrolysis activity. A phenomenon can be measured therewith in which a radioactively labeled organic substance such as sugar and amino acid is transported. An ion pump protein is a transporting carrier which transports sodium ions, potassium ions, hydrogen ions, calcium ions, etc., and transports the ions against the concentration gradient thereof. In order to transport the ion, it is necessary to supply a chemical energy obtained by the ATP decomposition, optical energy, etc.

Further, a receptor binds to a specific substance (ligand) such as a neurotransmitter, initiates the cell reaction, and can transform a signal outside a cell into a signal inside the cell.

An apparatus for the function analysis of biological membrane proteins for the purpose of the screening for drug discovery, elucidation of cell function, etc. can be manufactured by providing microelectrodes, by a common method, in such a bilayer membrane in which biological molecules are immobilized. The structure of the electrodes is not specifically limited. A method for detecting signals in parallel by a large number of electrodes arranged in parallel with a plurality of bilayer membranes which flow or stop in the microchannel (parallel detection with a large number of electrodes), or a method for detecting signals in series individually by successively passing a plurality of bilayer membranes through the electrode portion (sequential detection with a pair of electrodes) is commonly used.

The immobilization in a bilayer membrane is not limited to the above membrane proteins. Various substances can be incorporated according to the purpose. For example, an antigen can be detected by the change of the fluorescent intensity caused by the adsorption of the antigen on a fluorescent labeled antibody such as immunoglobulin. Hydrophilic ions can penetrate through a bilayer membrane if the bilayer membrane incorporates ionophores such as gramicidin, which is a peptide antibiotic produced by microorganisms, so that hydrophilic ions easily enter a hydrophobic phase of the bilayer membrane. For example, gramicidin A forms an ion channel in a membrane so that hydrogen ions, lithium ions, sodium ions, and potassium ions can penetrate.

The detection can be performed by a common method such as radioactive labeling and fluorescent labeling; and may be a measuring system using electricity, light, heat, etc.; and can be effectively used for the screening for drug discovery, antigen-antibody reaction analysis, etc.

Below, a device comprising a bilayer membrane of the present invention is explained in detail.

1. Device for a Membrane Protein Function Analysis

There are devices (A) for the purpose of the function analysis of a single membrane protein, and (B) for the purpose of the macroscopic behavior analysis with a large number of membrane proteins arranged on a planar bilayer membrane.

A formed planar lipid bilayer membrane is provided with a membrane protein to be investigated (ion channel, transporter, and receptor). Various physical or chemical stimulations are provided and the response of the membrane protein is measured.

Examples of the functions to be analyzed include single channel conductance, opening and closing time period, and open and close state probability, in the case of channel-forming membrane proteins. Examples of the stimulation include electrical stimulation in the case of voltage operated membrane proteins, ligand stimulation in the case of ligand operated membrane proteins, and mechanical stimulation in the case of mechanical stimulation operated membrane proteins. If the measuring means is an electrical measurement, the measuring object may be a membrane potential, single channel current, or gate current (voltage operated ion channel).

2. Sensor Device Using a Bilayer Planar Membrane (A) Bilayer Planar Membrane is Used as a Sensor (a) The confirmation of the incorporation of the substance into the lipid bilayer planer membrane, or (b) the detection and measurement, etc., of the substance contained in the water phase is performed by measuring the change in electrical response (lipid membrane potential, membrane current, membrane capacity, etc.) when a substance in the water phase is adsorbed on the formed planer lipid bilayer membrane. The substances included in the water phase may be various membrane proteins, or water-soluble environmental pollutants.

(B) Membrane Protein Embedded in a Bilayer Membrane is Used as a Sensor (1) Application of Ligand Operated Ion Channel The formed planar lipid bilayer membrane is provided with a receptor membrane protein. In a water phase, a ligand specific to the receptor (e.g., neurotransmitter emitted from nerve terminals, bioactive component emitted from secretory cells), or a substance capable of forming a ligand (e.g., nerve cells, secretory cells) is introduced, and the release or presence of the ligand is detected by detecting the response of the ligand due to the ligand binding. For example, a nicotinic acetylcholine receptor is an ion channel receptor (ligand operated ion channel), and the channel is opened by the binding of the ligand, i.e., acetylcholine. Accordingly, the release of the ligand can be detected in real time by measuring the current upon the opening of the channel. The release of acetylcholine can be detected in real time by providing the receptor in a planar lipid membrane, and introducing cells, which are a source for forming acetylcholine, into the water phase.

Similarly, the release of glutamic acid can be detected using a glutamic acid receptor as a sensor.

(2) Application of Other Ion Channels

A $Ca^{2+}$ activated $K^+$ channel exhibits the activity depending on the concentration of calcium inside cells. Therefore, the ion cannel can be used as a calcium sensor by providing the ion channel in a planar bilayer membrane.

Below, with reference to the drawings, the present invention is explained in more detail.

In FIG. 1, (a) is a conceptual diagram of the formation of a two phase plug flow, (b) and (c) are schematic diagrams showing the extraction of an organic phase and the production of a membrane using branch minichannels formed on the both side surfaces of a microchannel. (c) and (d) are schematic diagrams showing the extraction of an organic phase and the production of a membrane using branch minichannels formed on one side surface of a microchannel.

The state is formed where an organic phase (2) and a water phase (1) comprising amphipathic molecules are alternatively arranged inside the microchannel (3), (a). Then, the water phases (1) adjacent to each other are contacted by extracting the organic phase (2) into branch minichannels (4) formed on the side surface. Thereby a side-by-side arrangement of bilayer planar membranes comprising amphipathic molecules is formed ((b) to (e)).

An example using a T-shaped intersection is shown in (a). In the present invention, droplets of the same size at a regular interval can be formed, and the droplet size and formation interval can be precisely controlled by the control of the flow.

The amphipathic molecules are adsorbed on an interface between an organic phase—a water phase to form a monolayer membrane.

Then, the organic phase is extracted through branch minichannels (4) formed on (one or both) side surfaces of hydrophobic microchannel (3). The formation of thin membrane comprised of amphipathic molecules is promoted by contacting the water phases (1) adjacent to each other ((b) and (c)).

If biological molecules (e.g., membrane proteins) to be embedded in a lipid membrane have been preliminary incorporated in organic phase (2) or water phase (1), the biological molecules can be immobilized in the lipid membrane.

Figure 2:
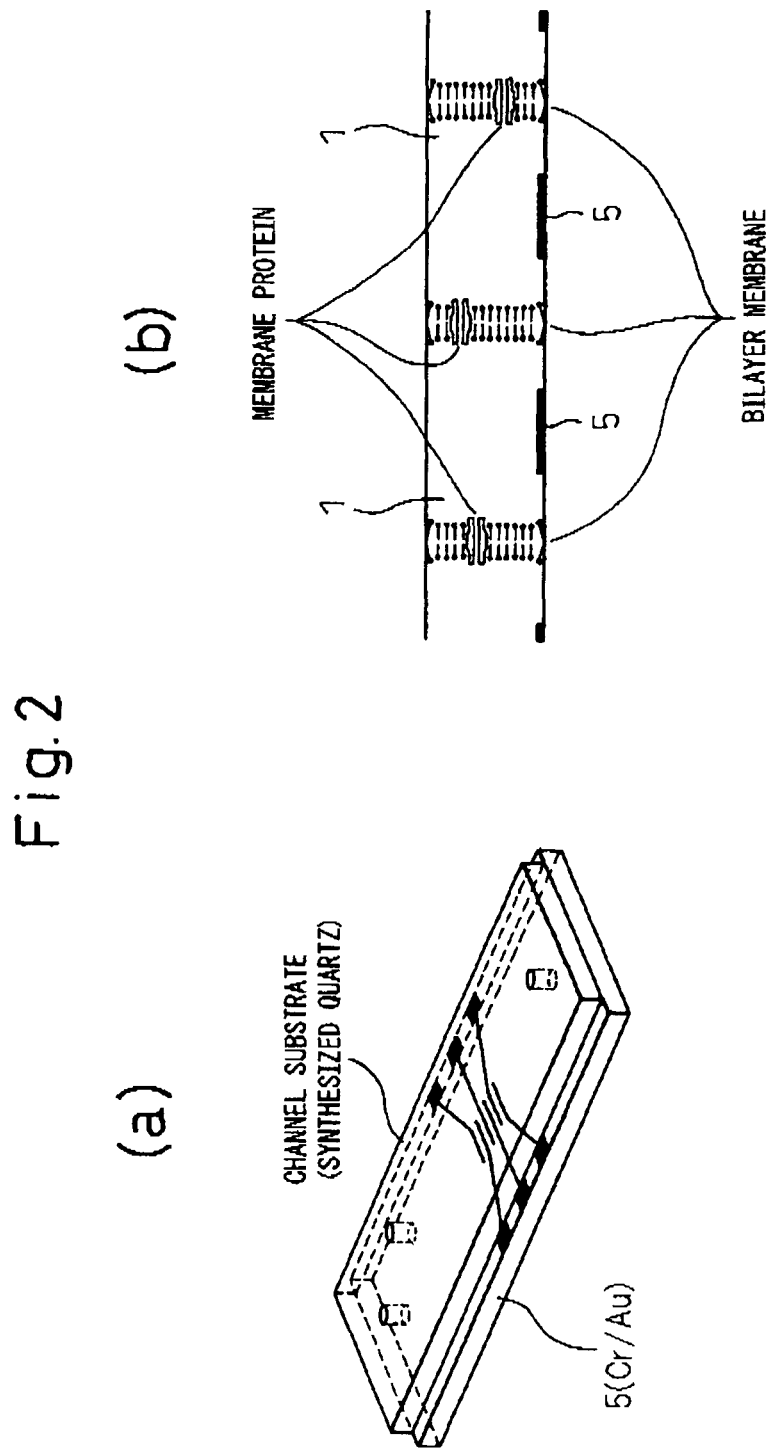
FIG. 2 shows one embodiment of a combination of microelectrodes and a microchannel.

FIG. 2 shows one embodiment of a combination of microelectrodes (5) and a microchannel (3). By the combination of microelectrodes (5) and a microchannel (3), the membrane thickness can be verified and the electrical response of the biological molecules can be measured.

Figure 3:
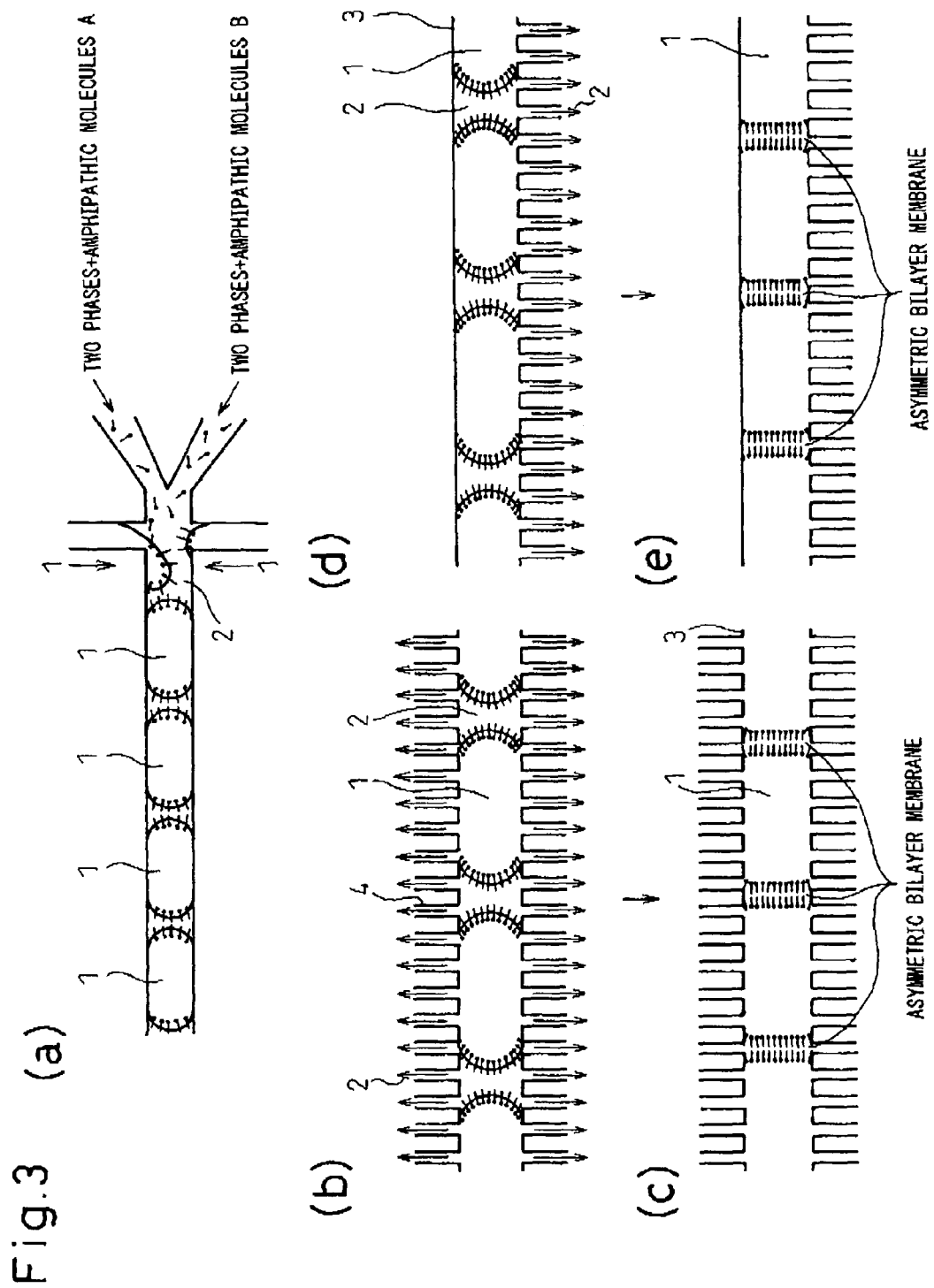
FIG. 3 shows one embodiment of a method for forming an asymmetric bilayer membrane.

FIG. 3 shows one embodiment of a method for forming an asymmetric bilayer membrane. (a) is a conceptual diagram of the formation of a two phase plug flow, (b) and (c) are schematic diagrams showing the extraction of an organic phase and the production of a membrane using branch minichannels formed on both side surfaces of a microchannel. (c) and (d) are schematic diagrams showing the extraction of an organic phase and the production of a membrane using branch minichannels formed on one side surface of a microchannel. According to the embodiment, it is possible to form an asymmetric bilayer membrane comprising different amphipathic molecules.

Below, with reference to the examples, the present invention is explained, but is not limited thereto.

EXAMPLE 1

Figure 4:
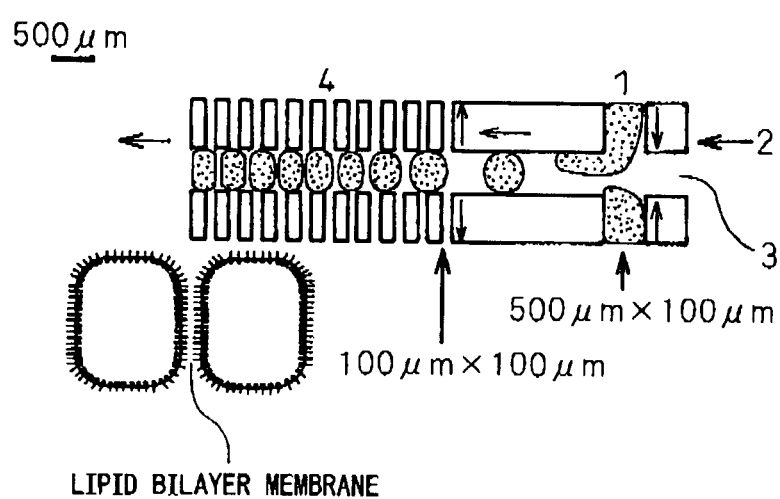
FIG. 4 shows a conceptual diagram of a procedure for forming lipid membranes.

A microchannel was fabricated in an acrylic resin (PMMA), and experiments were performed to form droplets and a side-by-side structure of lipid membranes. FIG. 4 is a conceptual drawing of the acrylic microchannel used and the procedure of lipid membrane formation.

Figure 5:
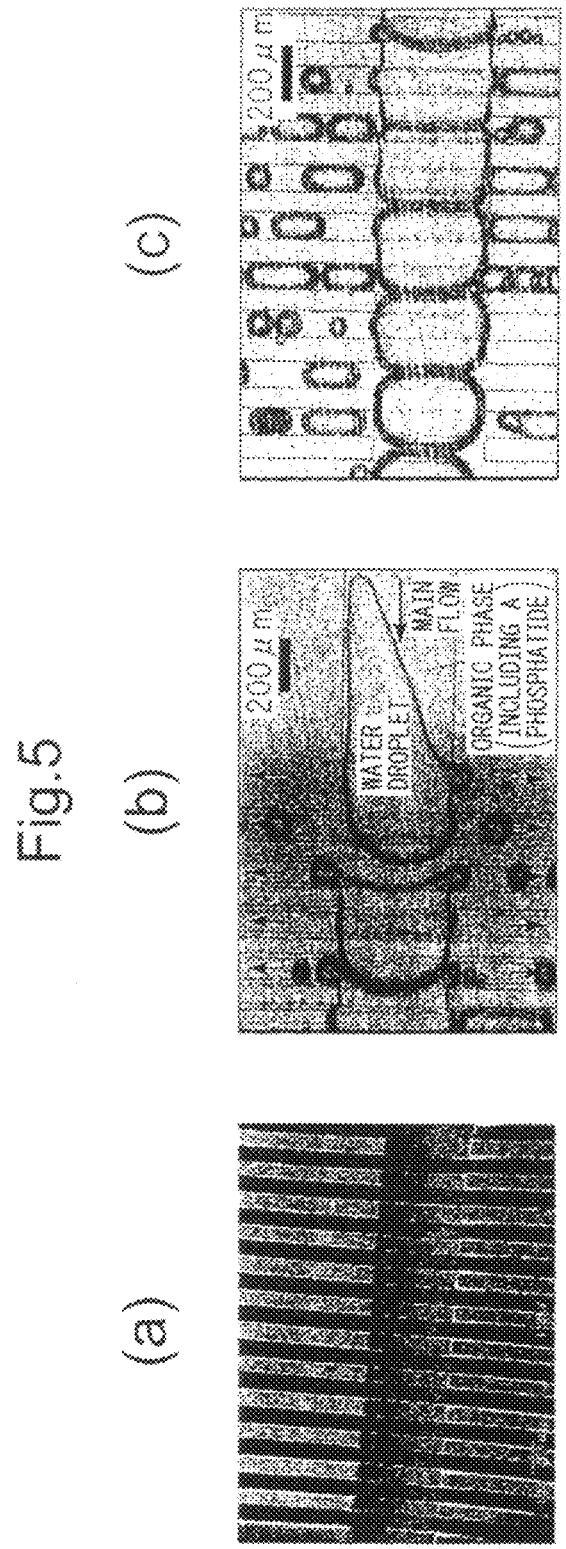
FIG. 5 shows one embodiment in which a side-by-side arrangement of lipid membranes is formed using an acrylic resin.

The branch structure of the microchannel (3) to form droplets is cross-shaped, 500 µm in width, and 100 µm in depth. The branch minichannels (4) for extracting an organic phase (2) have a size of a width of 100 µm, depth of 100 µm, and interval of 200 µm, and have a structure comprising a large number of the minichannels arranged side by side on the side surface of the microchannel (3). The microchannel was fabricated by a machining process, and sealed with a transparent adhesive tape to form a channel. Purified water was used as a dispersed phase (droplet-forming phase), and oleic acid (manufactured by Wako Pure Chemical Industries, Ltd.) dissolved with a phosphatide (dioleylphosphatidylcholine, DOPC, by Wako Pure Chemical Industries, Ltd.) at a concentration of 5 mg/ml was used as a continuous phase (surrounding the droplets). When the liquid continuous phase at 0.1 ml/hr and a dispersed phase and 0.05 ml/hr were liquid fed by a syringe pump (by KD scientific, KDS200), the formation of the droplets at regular intervals was able to be observed at the cross-shaped intersection. It was also observed that the organic phase (3) was collected by finer minichannels (3) (width 100 µm) formed downstream on both side surfaces, the anterior and posterior droplets contact each other, thereby a side-by-side arrangement of lipid bilayer membranes was formed. FIG. 5 shows one embodiment for forming a side-by-side arrangement of lipid membranes. (a) shows a SEM photograph of the channel having a depth of 100 µm, a width of 500 µm at a wide portion, and a width of 100 µm at a narrow portion (organic phase extraction channel), (b) shows the contact of water droplets, and (c) shows a side-by-side arrangement of lipid membranes formed by contacting a plurality of water droplets.

EXAMPLE 2

Figure 6:
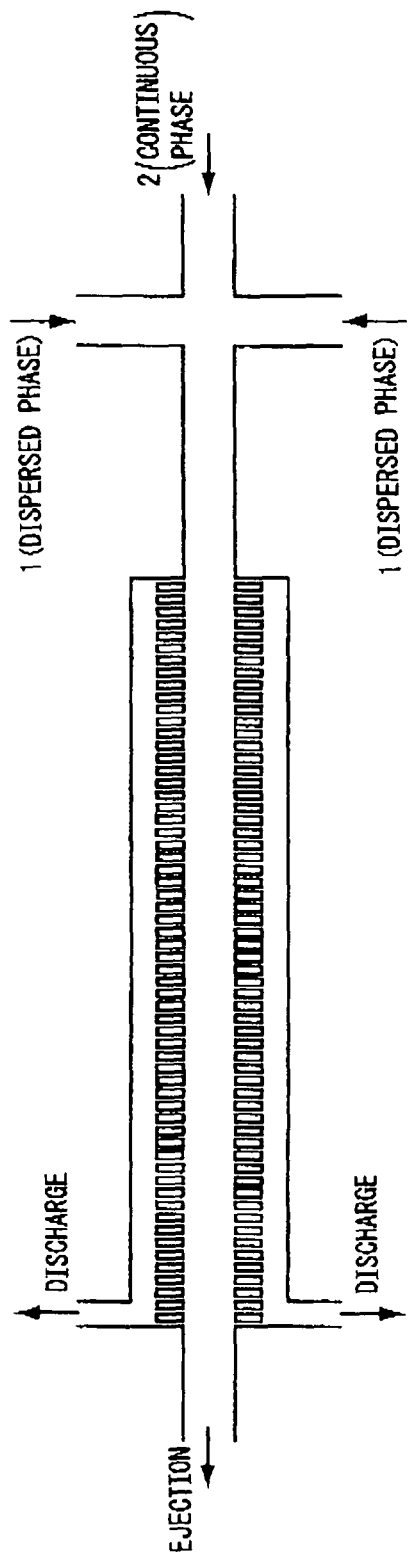
FIG. 6 shows a conceptual diagram of a microchannel and liquid feeding and discharging directions to form a side-by-side arrangement of lipid membranes.

A microchannel was processed in a fused silica glass substrate in a similar way to Example 1, water phase droplets and a side-by-side arrangement of lipid bilayer membranes were formed. FIG. 6 is a conceptual diagram showing a microchannel and the direction of liquid feed and the direction of discharge.

Figure 7:
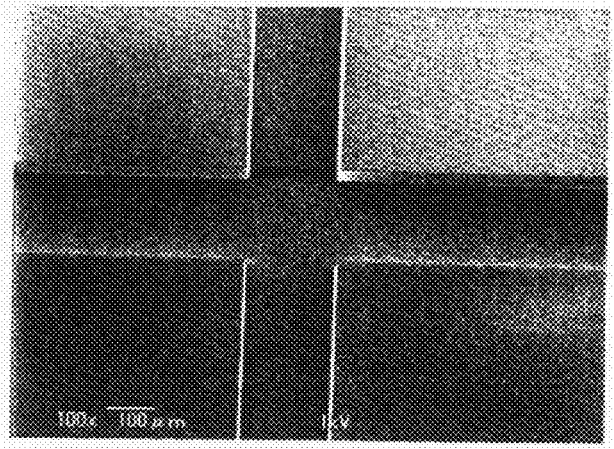
FIG. 7 shows a SEM (electron microscope) photograph of a cross-shaped intersection for forming droplets.
Figure 8:
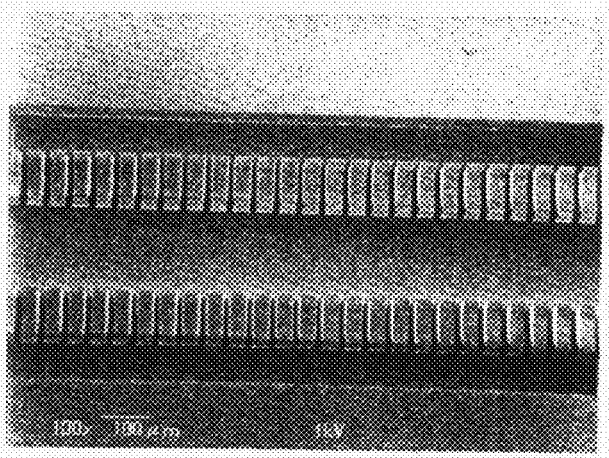
FIG. 8 shows a SEM photograph of a portion for the discharge of an organic phase and the formation of lipid membranes.

FIG. 7 is a SEM (electron microscope) photograph of a cross-shaped intersection for forming droplets. FIG. 8 is a SEM photograph of a portion for the discharge of the organic phase and the formation of lipid membranes. The branch structure of the microchannel for forming water phase droplets was cross-shaped as shown in FIG. 7, and the size thereof was 200 μm in width and 100 μm in depth. The portion for discharging the organic phase had a structure, as shown in FIG. 8, of a large number of minichannels for discharging the organic phase having a width of 20 μm, depth of 100 μm, and interval of 50 μm on both side surfaces of the microchannel for forming a lipid membrane having a width of 200 μm and a depth of 100 μm. The minichannels were fabricated by dry etching, and hermetically sealed by heat-adhering a thin sheet made of the same material (synthesized quartz). The channel made of fused silica glass originally had a hydrophilic surface and was not suitable for forming water droplets, without modifications. Therefore, the inner wall of the channel was subjected to a hydrophobic treatment with a hydrophobic treatment agent (Siliconise, manufactured by Fuji Systems Corporation) and thereafter the channel was used. Purified water was used as a dispersed phase (droplet-forming phase), and chloroform (by Wako Pure Chemical Industries, Ltd.) dissolved with a phosphatide (dioleylphosphatidylcholine, DOPC, manufactured by Wako Pure Chemical Industries, Ltd.) at a concentration of 5 mg/ml was used as a continuous phase (surrounding the droplets). The dispersed phase and the continuous phase were liquid fed by each syringe pump exclusive for liquid feeding. One syringe pump (by KD Scientific, KDS200) capable of a suction operation was used to discharge the continuous phase.

Figure 9:
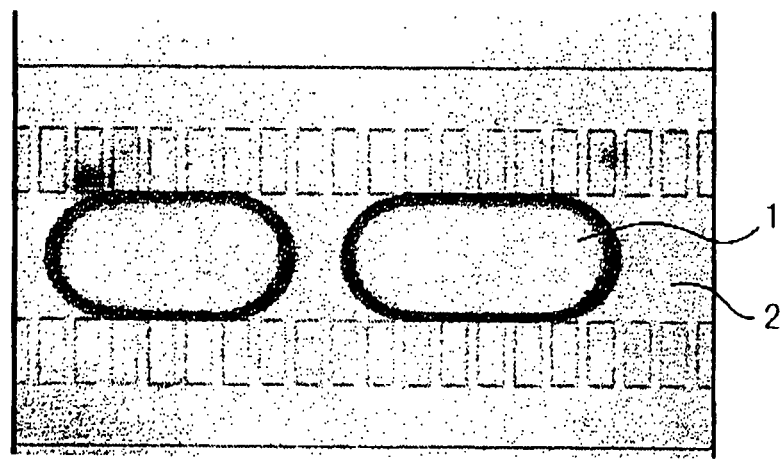
FIG. 9 shows an optical micrograph (10 fold magnification) showing purified water droplets in an organic phase.
Figure 10:
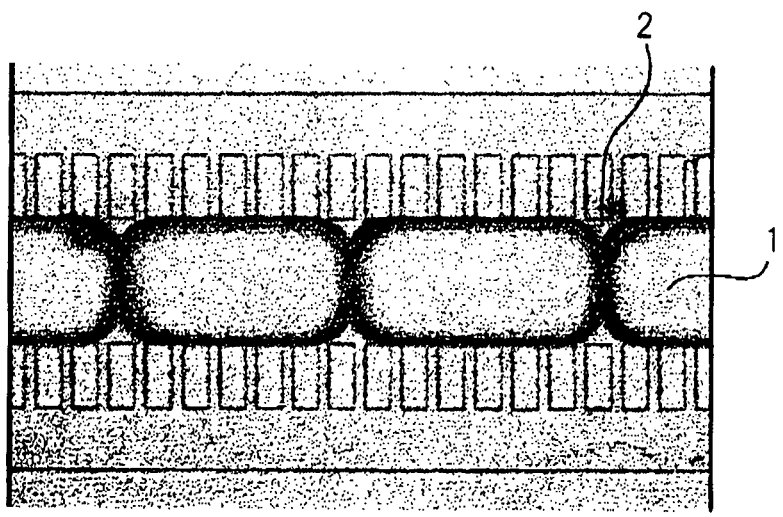
FIG. 10 shows an optical micrograph (10 fold magnification) showing a side-by-side arrangement of lipid membranes formed.

As shown by the optical microscope observation results (at 10 fold magnification) in FIG. 9, purified water droplets were formed at a regular interval in the organic phase at a cross-shaped intersection, when the liquid feeding rates of a water phase supplied from two directions were determined as 0.01 mL/hr each, the liquid feeding rate of an organic phase was determined as 0.1 mL/hr, and a discharge rates of the organic phase discharged in the two directions were determined as 0 mL/hr. At that time, water droplets flowed without contacting each other. Further, from the conditions, the discharge rates of the organic phase discharged in two directions were changed to 0.05 mL/hr (total 0.1 mL/hr), the water droplets formed at the cross-shaped intersection contacted each other at front and back ends to form a side-by-side arrangement of the lipid membranes as shown by the optical microscope observation results (at 10 fold magnification) in FIG. 10. No flow of water droplets into branch minichannels formed on both sides of the microchannel was observed.

Figure 11:
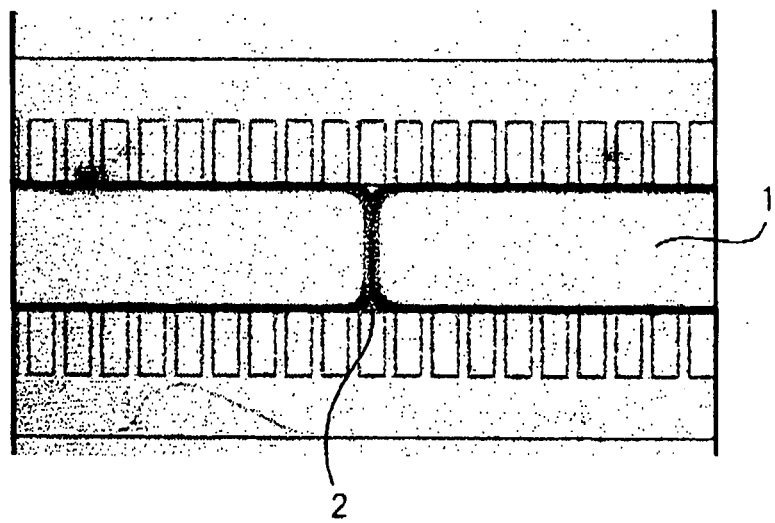
FIG. 11 shows an optical micrograph (10 fold magnification) showing a side-by-side arrangement of lipid membranes formed.
Figure 12:
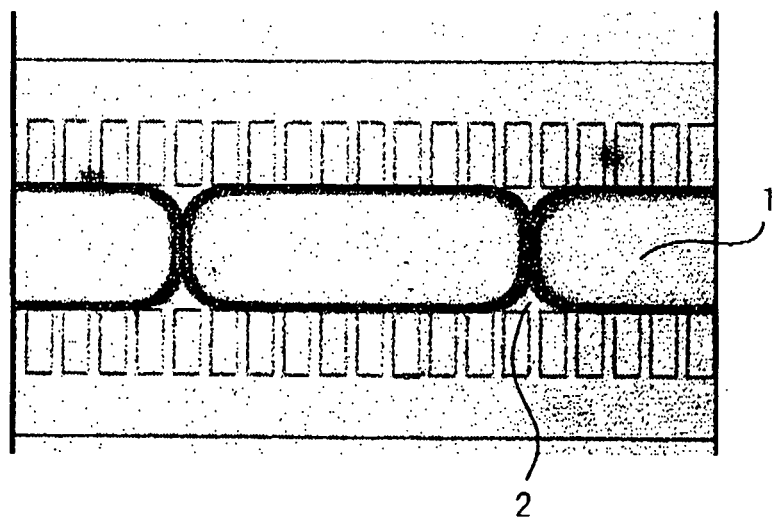
FIG. 12 shows an optical micrograph (10 fold magnification) showing a side-by-side arrangement of lipid membranes formed.
Figure 13:
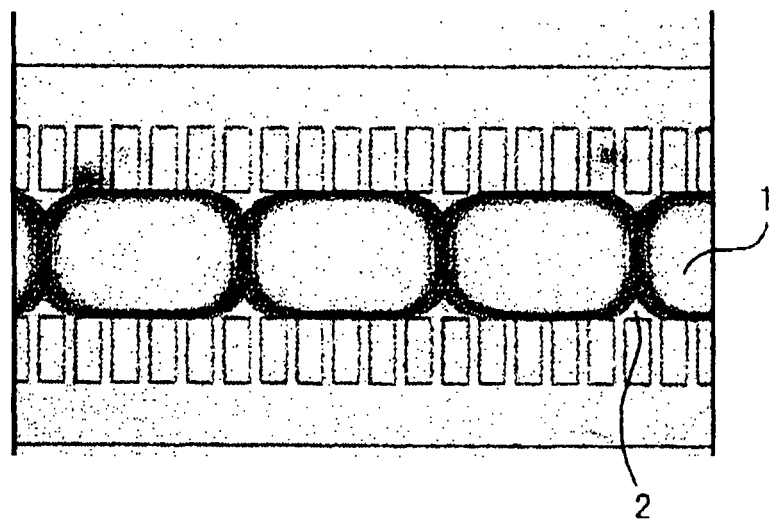
FIG. 13 shows an optical micrograph (10 fold magnification) showing a side-by-side arrangement of lipid membranes formed.

FIG. 11 (optical microscope observation (at 10 fold magnification)) shows the formation of a lipid membrane when the liquid feeding rates of a water phase supplied from two directions were determined as 0.01 mL/hr each, the liquid feeding rate of an organic phase was determined as 0.005 mL/hr, and the discharge rates of the organic phase discharged in the two directions were determined as 0.0025 ml/hr (total 0.005 mL/hr). FIG. 12 (optical microscope observation (at 10 fold magnification)) shows the formation of a lipid membrane when the liquid feeding rates of a water phase supplied from two directions were determined as 0.01 mL/hr each, the liquid feeding rate of an organic phase was determined as 0.01 mL/hr, and the discharge rates of the organic phase discharged in the two directions were determined as 0.005 mL/hr (total 0.01 mL/hr). FIG. 13 (optical microscope observation (at 10 fold magnification)) shows the formation of a lipid membrane when the liquid feeding rates of a water phase supplied from two directions were determined as 0.01 mL/hr each, the liquid feeding rate of an organic phase was determined as 0.5 mL/hr, and the discharge rates of the organic phase discharged in the two directions were determined as 0.25 mL/hr (total 0.5 mL/hr). In all cases, no flow of water droplets into branch minichannels formed on both side surfaces of the microchannel was observed. As clearly seen from FIGS. 10 to 13, it was possible to change an interval between lipid membranes by changing the flow rates.

EXAMPLE 3

Water phase droplets and a side-by-side arrangement were formed using a microchannel on a fused silica glass substrate. As a dispersed phase supplied from two directions at a cross-shaped intersection, purified water from one direction and purified water colored with aqueous blue ink from the other direction were used. As a continuous phase, chloroform (manufactured by Wako Pure Chemical Industries, Ltd.) dissolved with both a phosphatide (dioleylphosphatidylcholine, DOPC, manufactured by Wako Pure Chemical Industries, Ltd.) at a concentration of 5 mg/mL, and gramicidin A (manufactured by Calbiochem), which acts on ion penetration through cell membranes, at a concentration of 3 μg/mL was used. Other experimental configurations were similar to those of Example 2.

Figure 14:
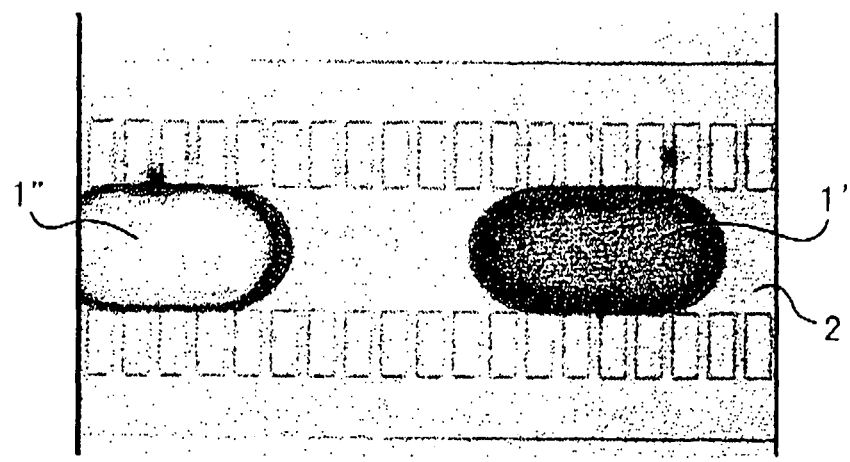
FIG. 14 shows an optical micrograph (10 fold magnification) showing an inside of a microchannel in Example 3.
Figure 15:
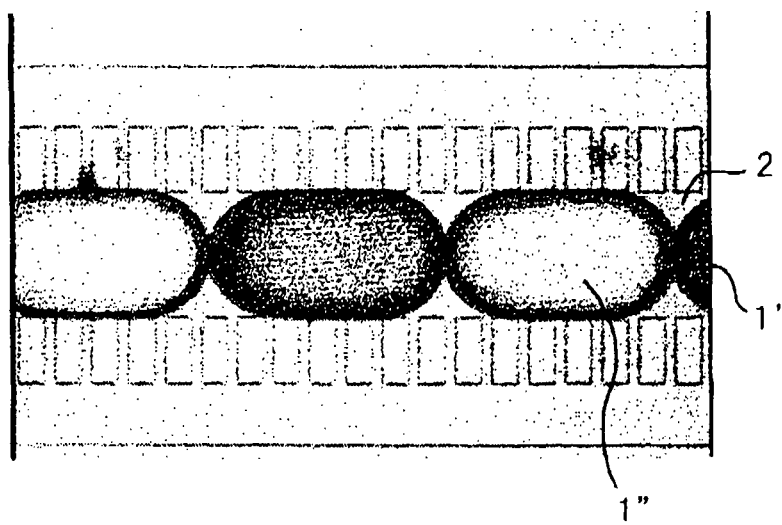
FIG. 15 shows an optical micrograph (10 fold magnification) showing a side-by-side arrangement of lipid membranes formed.
Figure 16:
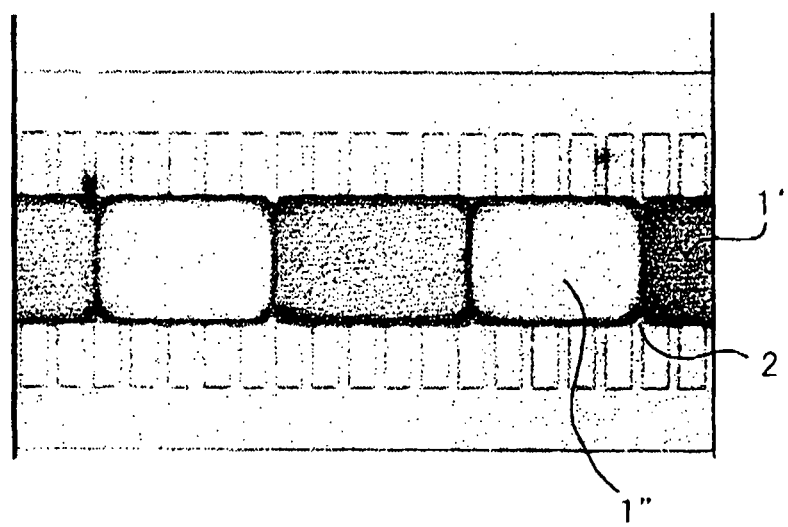
FIG. 16 shows an optical micrograph (10 fold magnification) showing a side-by-side arrangement of lipid membranes formed.
Figure 17:
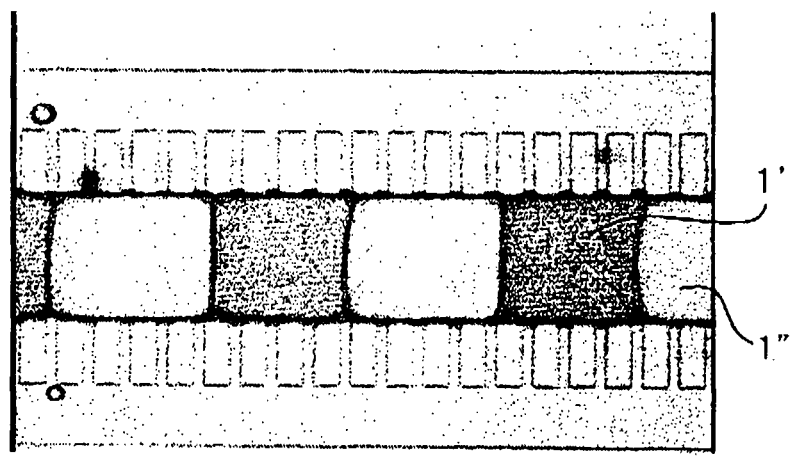
FIG. 17 shows an optical micrograph (10 fold magnification) showing a side-by-side arrangement of lipid membranes formed.

FIG. 14 (optical microscope observation (at 10 fold magnification)) shows the inside of a microchannel when the liquid feeding rates of a water phase supplied from two directions were determined as 0.01 mL/hr each, the liquid feeding rate of an organic phase was determined as 0.2 mL/hr, and the discharge rates of an organic phase discharged in the two directions were determined as 0 mL/hr each. In this case, blue-colored water phase droplets (blue droplets) (1') and colorless water phase droplets (colorless droplets) (1") were alternatively formed in the organic phase at regular intervals in the cross-shaped intersection. The formed blue water droplets (1') and colorless water droplets (1") flowed without contacting each other. Furthermore, from the conditions, the discharge rates of the organic phase discharged in two directions were increased to 0.11 mL/hr (total 0.22 mL/hr), as shown by the optical microscope observation results (at 10 fold magnification) in FIG. 16, and a contact area of droplets, i.e., a lipid membrane area increased. Then, the discharge rates of the organic phase discharged in two directions were increased to 0.115 mL/hr (total 0.23 mL/hr), as shown by the optical microscope observation results (at 10 fold magnification) in FIG. 17, and a contact area of droplets, i.e., a lipid membrane area further increased. As shown above, using an ionophore blended with an organic phase, a side-by-side arrangement of lipid membranes sandwiched with water phases each having a different component were formed. As just described, it was possible to change a lipid membrane area by changing a discharge rate of the organic phase.

INDUSTRIAL APPLICABILITY

The present invention can provide a process for forming a bilayer membrane with a microchannel capable of easily forming bilayer membranes such as planar lipid bilayer membranes in large quantities.

The invention claimed is:

1. A process for producing planar bilayer membranes, comprising:

forming a state where two liquid phases or liquid and gaseous phases each containing amphipathic molecules are alternately arranged as an array in a microchannel, discharging one of the two liquid phases or the gaseous phase of the liquid and gaseous phases from the microchannel through branch minichannels formed in the wall on one side or in the walls on both sides of the microchannel, so as to contact the remaining liquid phases adjacent to each other, and forming a side-by-side arrangement of planar bilayer membranes comprising the amphipathic molecules, wherein the planar bilayer membranes are independent from each other.

2. A process for producing bilayer membranes according to claim 1, comprising:

alternately introducing the two liquid phases or liquid and gaseous phases each containing amphipathic molecules using a branch structure of the microchannel to form the state where the two liquid phases or liquid and gaseous phases each containing amphipathic molecules are alternately arranged.

3. A process for producing bilayer membranes according to claim 2, wherein the branch structure of a microchannel is selected from a cross-shaped intersection, a T-shaped intersection, and a Y-shaped intersection.

4. A process for producing bilayer membranes according to claim 1, wherein the two liquid phases are an organic phase and a water phase.

5. A process for producing bilayer membranes according to claim 1, wherein the amphipathic molecules are a lipid, surfactant, or polymer.

6. A process for producing bilayer membranes according to claim 4, wherein the amphipathic molecules are introduced in admixture with the organic phase.

7. A process for producing bilayer membranes according to claim 1, wherein the amphipathic molecules are adsorbed on an interface of the organic phase and the water phase to form a monolayer membrane.

8. A process for producing bilayer membranes according to claim 4, comprising discharging the organic phase through branch minichannels formed in the wall on one side or in the walls on both sides of the microchannel, thereby bringing the adjacent water phases in contact with each other.

9. A process for producing bilayer membranes according to claim 4, comprising discharging the water phase through branch minichannels formed in the wall on one side or in the walls on both sides of the microchannel, thereby bringing the adjacent organic phases in contact with each other.

10. A process for producing bilayer membranes according to claim 1, wherein the discharge through branch minichannels is performed by capillary action through the branch minichannels and/or suction.

11. A process for producing bilayer membranes according to claim 1, wherein two or more bilayer membranes have the side-by-side arrangement at a constant interval.

12. A process for producing bilayer membranes according to claim 1, wherein the bilayer membranes are sandwiched with liquid phases having components different from each other.

13. An apparatus comprising a microchannel, and two or more planar bilayer membranes which are arranged as an array in said microchannel and contain amphipathic molecules, wherein each of the bilayer membranes contacts an organic phase or a water phase at both sides of the membrane, and wherein each of the bilayer membranes is sandwiched by mutually independent organic phases or water phases.

14. The apparatus according to claim 13, wherein each of the bilayer membranes is sandwiched by liquid phases having components different from each other.

15. The apparatus according to claim 13, wherein the amphipathic molecules are a phosphatide.

16. The apparatus according to claim 15, wherein a biological molecule is immobilized in the phosphatide.

17. The apparatus according to claim 16, wherein the biological molecule is a membrane protein.

18. The apparatus according to claim 17, wherein the membrane protein is selected from one or more of ion channel proteins, transporters, ion pump proteins, and receptors.

19. A device comprising the apparatus according to claim 15.

20. A device according to claim 19, wherein the device is adapted for a function analysis of membrane proteins.

21. A device according to claim 19, wherein the device is a sensor device.

* * * * *